United States Patent [19]
Kao et al.

[11] 4,093,649
[45] June 6, 1978

[54] LIQUID PHASE OXIDATION OF UNSATURATED ALDEHYDES TO CARBOXYLIC ACIDS WITH A BISMUTH CATALYST

[75] Inventors: Jar-lin Kao, Cherry Hill, N.J.; John Joseph Leonard, Springfield, Pa.

[73] Assignee: Atlantic Richfield Company, Los Angeles, Calif.

[21] Appl. No.: 766,112

[22] Filed: Feb. 7, 1977

[51] Int. Cl.$^2$ .............. C07C 51/32; C07C 57/04; C07C 57/06; C07C 57/08
[52] U.S. Cl. .................. 260/530 N; 260/526 N; 260/539 R
[58] Field of Search .......... 260/530 N, 526 N, 539 R

[56] References Cited

U.S. PATENT DOCUMENTS 2,212,900  8/1940  Groll et al. .................. 260/530 N

FOREIGN PATENT DOCUMENTS 373,326  5/1932  United Kingdom ............ 260/530 N

*Primary Examiner*—Vivian Garner
*Attorney, Agent, or Firm*—Delbert E. McCaslin

[57] ABSTRACT

A process for the preparation of $\alpha,\beta$-unsaturated aliphatic carboxylic acids by the liquid phase oxidation of the corresponding $\alpha,\beta$-unsaturated aliphatic aldehyde, such as acrolein and methacrolein, and the in situ decomposition or conversion of unsaturated peroxy (peroxide) compounds formed during oxidation, which comprises passing air or oxygen through an inert organic solvent solution of the aldehyde at a suitable temperature and pressure in the presence of a catalytic amount of an organic or inorganic bismuth salt. Heterogeneous solvent systems employing mixtures of the organic solvent and water may be used.

10 Claims, No Drawings

LIQUID PHASE OXIDATION OF UNSATURATED ALDEHYDES TO CARBOXYLIC ACIDS WITH A BISMUTH CATALYST

BACKGROUND OF THE INVENTION

A number of prior art processes have been proposed for the preparation of unsaturated carboxylic acids from their corresponding unsaturated aldehydes. Various catalytic vapor phase processes have been described. Liquid phase reactions include the use of hydroperoxides, molecular oxygen including air in the presence of various solvents and various organic and inorganic compounds of metals such as cobalt, combined with bromine compounds or chelates of a ketone, manganese, copper, nickel and vanadium, used singly and in combination. Generally the production of unsaturated aliphatic aldehydes in liquid phase has been difficult due to polymerization of the unsaturated acids when formed and the co-production of various undesirable peroxides of the unsaturated acids and aldehydes, resulting in low yield of the unsaturated acids.

To date no commercially successful process has been developed for the liquid phase preparation of unsaturated carboxylic acids, such as methacrylic acid, involving the in situ decomposition of peroxidic by products formed during the autoxidation of the aldehyde such as methacrolein. None of the above noted catalysts successfully decompose the peroxidic compounds in situ. The present process is directed to a much improved process for the preparation of unsaturated carboxylic acids in high yields and avoiding problems associated with the prior art processes. More particularly, the process relates to the synthesis of unsaturated carboxylic acids by the liquid phase solvent solution oxidation of the corresponding unsaturated aldehyde and the in situ conversion (decomposition) of the unsaturated peroxide compounds formed during said oxidation, by reacting the unsaturated aldehyde, and oxygen in a suitable solvent or mixture of solvents under moderate temperature and pressure conditions in the presence of a catalytic quantity of a bismuth salt compound.

U.S. Pat. No. 3,114,769 in an attempt to prevent polymeric by-products, describes a liquid phase process for the oxidation of methacrolein or acrolein to the corresponding acid and peroxide compounds in the presence of molecular oxygen and a small quantity of iodine. The products of the oxidation contained mixtures of unsaturated acids, and large amounts of both acid and aldehyde peroxides and unreacted aldehydes. The peroxide products were separately decomposed to the acid by the catalytic effect of a protonic acid such as p-toluene sulfonic acid and an alcohol forming a hot solvent solution as is further described in U.S. Pat. No. 3,253,025.

In an article by William F. Brill and Fred Lister, Journal of Organic Chemistry, Vol. 26, pp. 565–569, 1961 the metal-salt catalyzed oxidation of methacrolein in acetic acid is described. The methacrolein goes to peroxide products, acid and major amounts of soluble polymer.

The $\alpha,\beta$-unsaturated acid products obtained by the process of this invention have many known commercial uses, particularly for the preparation of esters such as methyl methacrylate or methyl acrylate and as monomers for polymer formation.

A particular advantage of the process of the present invention is the discovery that catalytic amounts of organic and inorganic bismuth salt compounds permit the intermediate peroxy compounds formed during oxidation of the unsaturated aldehydes, e.g., permethacrylic acid and methacrolein monopermethacrylate, which are formed during oxidation of methacrolein, to decompose or be converted to methacrylic acid, or other unsaturated acid and thus substantially increase selectivity to and yield of the particular unsaturated acid. Another advantage is that only small amounts of the bismuth compounds need be employed and much less peroxy (peroxide) compounds which might be formed need be removed from the reaction product and further processes thus providing a commercially attractive liquid phase process.

SUMMARY OF THE INVENTION

In accordance with the present invention, there is provided an improved process for the catalytic liquid phase oxidation of $\alpha,\beta$-unsaturated aliphatic aldehydes to the corresponding $\alpha,\beta$-unsaturated aliphatic carboxylic acids in high yield by reacting the unsaturated aldehyde with oxygen in a suitable inert solvent, which process is carried out at relatively moderate temperatures and pressures in the presence of a catalytic amount of a bismuth salt catalyst compound or mixtures thereof, which promote the decomposition or conversion of intermediate peroxides formed by the oxidation, to provide a pronounced effect on unsaturated acid selectivity as compared to known liquid phase processes.

It is a primary object of this invention to provide an improved process for the liquid phase preparation of $\alpha,\beta$-unsaturated aliphatic acids such as methacrylic acid in high yield while avoiding operational problems associated with prior liquid phase processes for the oxidation of unsaturated lower aliphatic aldehydes.

It is another object of this invention to provide a novel reaction system useful for the in situ decomposition of co-produced peroxide compounds to the desired unsaturated acid, thereby preventing a build up of peroxide compounds during the autoxidation of the aldehyde.

It is a further object of this invention to provide a specific catalytic mechanism for the employment of bismuth salt compounds in various solvent systems employing unsaturated lower aliphatic aldehydes and oxygen as reactants.

These and other objects and advantages of this invention will become apparent from the description of the invention which follows and from the claims.

DESCRIPTION OF THE INVENTION

According to the invention a process has been discovered in which $\alpha,\beta$-unsaturated aliphatic acids are prepared by the liquid phase oxidation of the corresponding $\alpha,\beta$-unsaturated aliphatic aldehydes and the in situ conversion or decomposition of corresponding peroxy compounds which are formed as a result of the oxidation reaction. The oxidation reaction is carried out at suitable temperatures and pressures in a suitable inert solvent in the presence of and under the catalytic effect of an organic or inorganic bismuth salt compound in which the bismuth may be in the $Bi^{+3}$ or $Bi^{+5}$ oxidation state.

When unsaturated aliphatic aldehydes, such as methacrolein, are oxidized in the liquid phase with oxygen or an oxygen-containing gas, a mixture of products is obtained in the oxidate reaction product. The oxidate will generally contain some unreacted aldehyde, some of the corresponding peroxy (peroxide) compounds of the unsaturated aldehyde feed materials and the unsaturated acid product. For example, the peroxy (peroxide) compounds co-produced in the autoxidation of methacrolein and crotonaldehyde would be permethacrylic acid and methacrolein monopermethacrylate and percrotonic acid and crotonaldehyde monopercrotonate respectively. Similar corresponding peroxy compounds would be produced with other unsaturated aldehydes such as acrolein, which may be employed in the process of this invention.

The preferred $\alpha,\beta$-unsaturated aliphatic aldehydes which may be employed as starting materials in this invention are the unsaturated lower aliphatic aldehydes, particularly the $\alpha,\beta$-unsaturated aldehydes having from 3 to 6 carbon atoms. Representative aldehydes include, for example, acrolein, methacrolein, ethacrolein, crotonaldehyde, alpha-chloroacrolein, 3-methylcrotonaldehyde, 2-methylpentaldehyde and the like. Representative unsaturated acids produced by the process of this invention are, for example, acrylic acid, methacrylic acid and crotonic acid from acrolein, methacrolein and crotonaldehyde respectively.

The process of the invention may be carried out batchwise, semi-continuous or continuous in any suitable reactor such as a glass or aluminum reactor or autoclave. Although the order of addition of reactants and catalyst may vary somewhat, a general procedure is to charge the unsaturated aldehyde dissolved in a suitable solvent along with the catalyst into the reaction vessel which is equipped with a means for agitation of the liquid, and then introduce the proper amount of oxygen to the desired reaction pressure and heat the mixture if necessary to the desired temperature for the appropriate period. The reaction products are recovered and treated by any conventional method such as for example, by distillation, by extracting the acid with a base and subsequent acidification, or by solvent extraction.

Since the catalytic oxidation process of the present invention is a free radical reaction, it is desirable that apparatus unlikely to cause problems with such reaction mechanisms be selected and any active sites which may be on the reactor surface and which may cause adverse catalytic activity under reaction conditions be passified or neutralized to render the surface essentially inert. Free radical reactions may be sensitive to the active material (active sites) of the reactor surface. Thus, the apparatus is preferably, for example, constructed of glass, titanium, polymeric materials such as polytetrafluorethylene (Teflon) or aluminum which desirably is treated by known methods for example, by washing the surfaces with hot hydrogen peroxide and/or with a sodium pyrophosphate solution or other chelating agents.

The catalytic bismuth salt compounds or mixtures of compounds which may be employed in the process of this invention for the liquid phase oxidation of aliphatic unsaturated aldehydes and the in situ decomposition or conversion of the intermediate peroxy compounds, to the corresponding aliphatic unsaturated carboxylic acid may be organic or inorganic bismuth compounds. Representative chemical forms of the bismuth salt compounds which can be used as such or as mixtures or formed in the reaction system from the bismuth metal are, for example, organic bismuth compounds such as bismuth citrate, bismuth oleate, bismuth tartrate, bismuth phenate, bismuth ammonium citrate, etc. and inorganic bismuth compounds such as bismuth chloride, bromide, iodide, oxide, nitrate, sulfate, carbonate, etc., as well as bismuth pentafluoride, bismuth pentoxide, etc. As indicated above, the bismuth metal may be added to the reaction, a salt compound being formed in situ from at least a portion of the metal under reaction conditions, for example, bismuth oxide.

The bismuth salt compounds employed may be in a homogeneous state in the reaction mixture at reaction conditions. Thus, the compounds may be present in solution, or suspension and may also be on support materials which will not affect the reaction such as alumina, silica gel, aluminosilicates, activated carbon or zeolites. The compounds may be partially or completely soluble under reaction conditions and are preferably in a finely divided state. The reaction is carried out in the presence of a catalytic proportion of the bismuth salt compound and will proceed with small amounts of the representative compounds hereinabove described. Generally the proportions of the bismuth salt compound used in the reaction will be equivalent to between about 0.00001 to 0.5 mole and preferably in amounts between about 0.001 to 0.01 mole of bismuth salt compound per mole of the unsaturated aldehyde employed. In the absence of the catalytic quantities of the bismuth salt compounds only a small amount of in situ decomposition or conversion of the intermediate peroxides occurs.

The reaction is conducted in the liquid phase in which the aldehyde is dissolved in an inert organic solvent or mixture of solvents. The concentrations of unsaturated aldehyde in the mixture of solvents and aldehyde may be between about 5 per cent and 90 per cent and preferably between about 20 per cent and 80 per cent by weight of the aldehyde-solvent solution.

The solvents employed in the process of the invention must be inert under the reaction conditions used, i.e., non-reactive under the certain process conditions used, and preferably should be easily separable from the reaction mixture and components thereof including the aldehyde starting material, any intermediate products and acid product.

The solvents which may be employed in concentrations of from about 10 to 95 weight per cent, preferably 20 to 80 weight per cent, of the solvent-aldehyde mixture and suitable for use in the process of the present invention can be aliphatic, cycloaliphatic and aromatic hydrocarbons and chlorinated hydrocarbons including halogenated aromatic hydrocarbons, carboxylic acids, ethers, esters and amides. Certain inert tertiary alcohols such as tertiary octyl alcohol, may also be employed. Representative solvents especially suitable for use in this invention include benzene, toluene, o-, m-, and p-xylenes, hexane, cyclohexane, ethylcyclohexane, chlorobenzene, bromobenzene, chlorotoluene, carbon tetrachloride, chloroform, methylene chloride, acetic acid, ethyl acetate, butyl acetate, methyl acetate, cyclohexyl acetate, methyl benzoate, tetrahydrofuran, dioxane, dimethylformamide, N,N'-dimethyl acetamide, etc. While solvents or mixtures of solvents are preferably employed in the process of this invention, some of the aldehydes which may be employed may be oxidized in the presence of catalytic amounts of the bismuth salt compounds without the use of a solvent particularly if the bismuth compound is essentially soluble in the aldehyde.

The above solvents which may be employed in the process of the invention may also be mixed with water forming a heterogeneous solvent system. The water may amount to as low as about 5 per cent or as much as 95 per cent by weight of the reaction medium solvent solution and preferably ranges between about 30 to 60 per cent by weight of the total solvent solution employed. While water may possibly be used as the sole liquid component the essential purpose of employing a co-solvent, hydrocarbons, esters, etc., is to increase the solubility of the unsaturated aldehyde being employed.

The oxygen-containing gas employed in carrying out the oxidation process of the instant invention is generally oxygen itself or air. Air is included by the phrase "oxygen-containing gas" as are relatively pure oxygen gas and other oxygen-containing gases. Oxygen itself may be diluted with an inert gas such as nitrogen, carbon dioxide or helium.

The reaction is conducted at moderate temperatures, generally between 0° C. and 100° C. and preferably at temperatures of from about 20° C. to 80° C. and under sufficient pressure to maintain a liquid reaction phase. The reaction may be carried out at higher or lower temperatures with superatmospheric or subatmospheric pressures. The reaction may be carried out at atmospheric pressure and pressures of up to about 1500 psig may be employed. Elevated pressures of from about 50 psig to about 500 psig are particularly advantageous. When using an unsaturated aldehyde and/or solvent which may be relatively volatile, elevated pressures may be necessary to ensure reaction in the liquid phase.

Generally the reaction time may vary between a few minutes and several hours and is generally dependent on the aldehyde being reacted, temperature and pressure as well as the equipment being employed. Reaction times may vary dependent on whether the process is continuous or batch. The following examples are provided to illustrate the invention in accordance with the principles of this invention but are not to be construed as limiting the invention in any way except as indicated by the appended claims. Unless otherwise noted, percentages are in terms of per cent by weight.

In the Examples which follows, a cylindrical aluminum reactor having a 45 ml. capacity was treated with hot (80° C.) 30 per cent hydrogen peroxide, rinsed with acetone, dried in air and the aldehyde, the bismuth salt catalyst and solvent charged to the reactor. The mixture was agitated by a magnetic stirring rod at the indicated reaction temperatures under oxygen pressure. Upon completion of the reaction, the mixture was cooled in a dry ice-isopropanol bath and the pressure slowly vented. To prevent polymerization of the reaction products, during recovery, 0.1 g. of 2,6-di-tert-butyl-4-methylphenol was added.

The catalysts, solvents, reaction conditions and results are summarized in the following Table. Example 1 is a comparative example with no catalyst employed.

Analysis of the reaction product solutions were conducted as follows: A sample was titrated by differential potassium iodide to determine permethacrylic acid and methacrolein monopermethacrylate or other peroxy compounds produced as intermediate compounds during the oxidation of aldehydes other than methacrolein. Another sample was reduced with triphenylphosphine and analyzed by gasliquid chromatography to determine the aldehyde, carboxylic acid and other products. A third sample was titrated by potassium hydroxide to determine total acidity.

In the Examples the following abbreviations are used:
MA — methacrolein
MAA — methacrylic acid
MMPM — methacrolein monopermethacrylate
$BiC_6H_5O_7$ — bismuth citrate
% MA Conv. — per cent methacrolein conversion
PMAA — permethacrylic acid

TABLE

Autoxidation of Methacrolein — 30 per cent MA in Solvent

| Example | Catalyst | Solvent (g.) | Wt. % Conc. of Catalyst | MA (g) | Temp. ° C. | $O_2$ Pressure (psig) | Time (min.) | % MA Conv. | % Selectivity To MAA | PMAA | MMPM | Other By-Products[3] |
|---|---|---|---|---|---|---|---|---|---|---|---|---|
| 1 | none | n-hexane (4.50g.) | — | 2.0 | 40 | 100 | 115 | 35 | 21 | 6 | 47 | 26 |
| 2 | $BiCl_3$ | n-hexane (4.50 g.) | 0.18 | 2.0 | 40 | 100 | 90 | 32 | 31 | 7 | 38 | 24 |
| 3 | $BiC_6H_5O_7$ | benzene (4.50 g.) | 0.30 | 2.0 | 50 | 100 | 80 | 34 | 35 | 5 | 35 | 25 |
| 4 | $Bi(NO_3)_3$ | dioxane (4.00 g.) | 0.56 | 2.0 | 60 | 100 | 50 | 31 | 40 | 2 | 31 | 27 |
| 5[1] | $BiC_6H_5O_7$ | n-hexane (4.50 g.) | 0.28 | 2.0 | 40 | 100 | 100 | 33 | 51[2] | 1 | 20 | 28 |

[1] 2.0 g. acrolein employed as aldehyde — 30 per cent by weight in solvent.
[2] acrylic acid as product and corresponding peroxy compounds.
[3] includes acetic acid produced.

We claim:

1. A process for the liquid phase oxidation of an α,β-unsaturated aliphatic aldehyde containing from 3 to 6 carbon atoms in an inert solvent solution to the corresponding unsaturated aliphatic carboxylic acid which comprises contacting said aldehyde with oxygen or an oxygen-containing gas at a temperature of from about 0° C. to 100° C. and a pressure between about atmospheric and 1500 psig in the presence of from about 0.00001 to 0.5 mole of an inorganic or organic bismuth salt catalyst selected from the group consisting of bismuth chloride, bismuth bromide, bismuth iodide, bismuth oxide, bismuth nitrate, bismuth sulfate, bismuth carbonate, bismuth pentafluoride, bismuth pentoxide, bismuth citrate, bismuth oleate, bismuth tartrate, bismuth phenate and bismuth ammonium citrate or mixtures thereof, per mole of said aldehyde to effect an in situ decomposition of intermediate peroxide compounds formed during the oxidation to said unsaturated aliphatic carboxylic acid.

2. A process according to claim 1 wherein the aldehyde is selected from the group consisting of acrolein and methacrolein.

3. A process according to claim 2 wherein the aldehyde is methacrolein.

4. A process according to claim 1 wherein the inert solvent is employed in concentrations of from about 10 to 95 weight per cent of the solvent-aldehyde mixture and is selected from the group consisting of aliphatic, cycloaliphatic and aromatic hydrocarbons, carboxylic acids, ethers, esters and amides or mixtures thereof.

5. A process according to claim 4 wherein the concentration of solvent is from about 20 to 80 weight per cent and the solvent is selected from the group consisting of n-hexane, benzene and dioxane.

6. A process according to claim 1 wherein the temperature is in the range of from about 20° C. to 80° C. and the pressure is between about 50 psig and 500 psig.

7. A process according to claim 1 wherein from about 0.001 to 0.01 mole of bismuth salt catalyst per mole of aldehyde is employed.

8. A process according to claim 1 wherein air is employed as the oxygen-containing gas.

9. A process according to claim 1 wherein the bismuth salt catalyst is supported.

10. A process for the liquid phase oxidation of methacrolein in an inert solvent solution to the corresponding methacrylic acid which comprises contacting said methacrolein with oxygen or an oxygen-containing gas at a temperature of from about 20° C. to 80° C. and a pressure of between about 50 psig and 500 psig in the presence of from about 0.001 to 0.1 mole of an inorganic or organic bismuth salt catalyst selected from the group consisting of bismuth chloride, bismuth bromide, bismuth iodide, bismuth oxide, bismuth nitrate, bismuth sulfate, bismuth carbonate, bismuth pentafluoride, bismuth pentoxide, bismuth citrate, bismuth oleate, bismuth tartrate, bismuth phenate and bismuth ammonium citrate or mixtures thereof, per mole of methacrolein to effect an in situ decomposition of intermediate permethacrylic acid and methacrolein monopermethacrylate formed during the oxidation to said methacrylic acid.

* * * * *